United States Patent [19]

Moedritzer

[11] 4,087,408
[45] May 2, 1978

[54] BROMINE AND PHOSPHORUS CONTAINING POLYESTER

[75] Inventor: Kurt Moedritzer, Webster Groves, Mo.

[73] Assignee: Monsanto Company, St. Louis, Mo.

[21] Appl. No.: 750,756

[22] Filed: Dec. 15, 1976

[51] Int. Cl.² .................. C08G 63/18; C08G 63/68
[52] U.S. Cl. ..................... 260/47 P; 260/47 C; 260/75 P; 260/606.5 P
[58] Field of Search ............. 260/606.5 P, 47 C, 47 P, 260/75 P, 61

[56] References Cited

U.S. PATENT DOCUMENTS

| | | | |
|---|---|---|---|
| 3,376,258 | 4/1968 | Gysling et al. | 260/47 |
| 3,928,283 | 12/1975 | Masai et al. | 260/45.7 P |
| 3,993,623 | 11/1976 | Moedritzer et al. | 260/45.95 P |

Primary Examiner—Lester L. Lee
Attorney, Agent, or Firm—Herman O. Bauermeister

[57] ABSTRACT

Polyesters containing bromine and phosphorus are provided by the copolymerization of a ternary system based upon an alcoholic component and an acidic component. The third component is a bromo bisphenol alkyl or aryl phosphine oxide

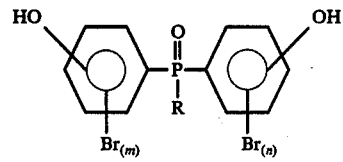

The hydroxyl groups are present in either the para or meta positions, $m$ plus $n$ is from 1 to 8, preferably 1 to 4 and R is an alkyl radical of 1–10 carbon atoms, or an aryl radical of 6–10 carbon atoms. The polyesters which are obtained have flame retardant properties.

8 Claims, No Drawings

BROMINE AND PHOSPHORUS CONTAINING POLYESTER

BACKGROUND OF THE INVENTION

The present invention relates to flame retardant compositions which are bromine and phosphorus containing polyesters, and which are particularly adapted to prevent crystallization, and exuding or oiling out such as occurs in other flame retardant methods. The present organic polymer compositions are ternary copolymers in which a bromo bisphenol alkyl or aryl phosphine oxide replaces a portion of the hydroxy component of the polyester.

Compounds of various types have been employed as flame retardant components, generally as physical additives, in various organic polymers. However, a common difficulty when using such compounds has been their incompatibility with the organic polymer base material; for example, some inorganic phosphates such as ammonium phosphate when used in polyethylene terephthalate. Other additives including organic phosphates have been found to exude out of the polymer so that the desired flame-retardant modifying effect on the organic polymer was lost.

The present ternary polymeric esters are based upon an alcoholic component such as ethylene glycol and an acidic component such as terephthalic acid. Derivatives of each of these compounds are also used in the same relationship. However, a third component, copolymerized as a part of the final ester is also present, namely bromobisphenol alkyl or aryl phosphine oxide.

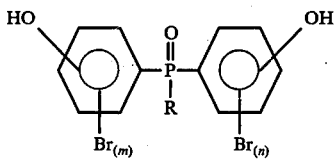

The hydroxyl groups are present in either P or m positions rel. to phosphorus, $m$ plus $n$ is from 1 to 8, preferably 1 to 4 and most preferably 4, and R is an alkyl radical of 1 to 10 carbon atoms, or an aryl radical of 6 to 10 carbon atoms. This bromine and phosphorus containing compound provides a synergistic flame retardant effect, while at the same time permitting the poylester to be formed by the usual polymerization and other processing steps without deleterious effects upon the fiber properties. The above products are compounds with both phosphorus and bromine present in the same molecule. These compounds are bifunctional components which copolymerize as a stable, non-degrading polymer. The prior art has used individual phosphorus and bromine components, but many of these degraded or separated out of the fiber. In contrast, the present fibers avoid crystallization of a solid phase which would prevent spinning by clogging the spinnerettes. The polyester product also retains the other desirable properties of high strength, as well as wash and wear characteristics, e.g. retention in the copolymer without washing out. The polyesters lend themselves very well to blend fabrics such as polyester/cotton and exhibit good hand and other esthetic properties. The polyester fibers also avoid degradation of the polyester so that the molecular weight is retained with good spinnability.

The resultant ternary polymers have at least 2 wt. % bromine, and preferably from 3 to 25 wt. % bromine and 0.1 to 10 wt. % phosphorus based upon the total polymer. A preferred range of phosphorus is from 0.5 to 1.5%. Control of the relative proportions of the alcohol and of the acid moieties as well as the relative molecular weight of the starting materials and of the final polymeric esters makes it possible to obtain products having properties of solubility, and melting point to provide flame retardant properties and other physical properties without the prior art difficulties of exuding or crystallization.

SUMMARY OF THE INVENTION

In accordance with the present invention a process of esterification is employed to form new phosphorus and bromine containing polyesters having at least 2 wt. % or preferably from 3 to 25 wt. % bromine in the polyester. The proportion of phosphorus is from 0.1–10 wt. %. The reactants are;

a. an aliphatic alcohol of 2 to 20 carbon atoms such as ethylene glycol, propylene glycol, butylene glycol, hexylene glycol, decylene glycol and dodecylene glycol.

b. The second component is a dicarboxylic aliphatic or aromatic acid of 8 to 20 carbon atoms such as terephthalic acid, iso-phthalic acid, hexahydroterephthalic acid, naphthalene dicarboxylic acid (1,5-, 2,6-, or 2.7), bi-benzoic acid, sebacic acid or succinic acid. However, esters of the dicarboxylic acids such as dimethyl terephthalate may be used as reactants in the present esterification.

c. The third component is a brominated bisphenol alkyl or aryl phosphine oxide

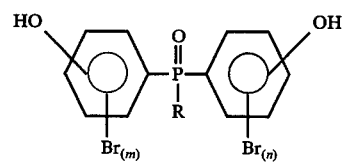

The hydroxyl groups are present in either the para or meta positions, $m$ plus $n$ is from 1 to 8, preferably 1 to 4, and R is an alkyl radical of 1 to 10 carbon atoms, or an aryl radical of 6 to 10 carbon atoms. The bisphenol may be acetylated or hydroxyethylated.

To give the following compounds, respectively, for use in copolymerization

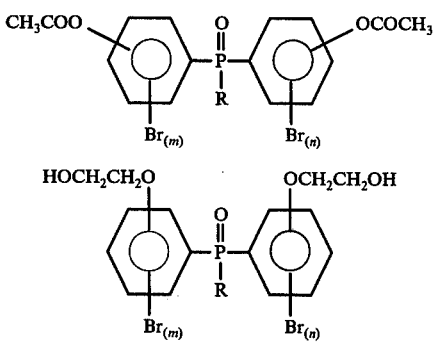

The ternary polyesters of the present invention have substantially stoichiometric proportions of the alcoholic component (a) and the acidic component (b), although an excess of the alcoholic or glycol component is generally employed in the process. The brominated phosphorus compound (c) is used as the equivalent of the alcoholic component, and with the final proportions of bromine and phosphorus in the polyester as set forth above.

In general, the brominated phosphorus compound is used in the range of 1 to 20 wt. % of the ternary copolymer. The polyester is thus based upon the dicarboxylic acid in approximately stoichiometric relationship with the glycol, with the proviso that part of the glycol is substituted by an equivalent amount of the brominated bisphenol alkyl or aryl phosphine oxide.

The ternary components are first esterified or condensed, and then further polymerized. The general term employed for this process is copolymerization.

The copolyesters of the present invention are formed in the following manner. Typically, the aromatic dicarboxylic acid member and the glycol member are refluxed at elevated temperatures, such as 200° C to 300° C preferably at about 200°–225° C in the presence of a catalyst until the theoretical yield of the condensation or ester interchange product liberated is distilled off. Heating is then continued under reflux at about 225°–250° C to raise the molecular wt. of the polyester. During the polymerization the pressure is gradually reduced to about 0.5–30mm Hg, or preferably 1–20mm Hg, and the ingredients are heated to and maintained at about 225°–270° C for about 2-6 hours.

Various catalysts can be used in connection with the various reactions. For example, the first condensation reaction between the aromatic dicarboxylic acid member and the glycol member may be catalyzed by individual catalysts such as antimony trioxide, litharge, zinc acetate, lead acetate, or manganese acetate or dibutyltin oxide/antimony trioxide or by any of the other conventional polyesterification catalysts. Similarly, the second condensation reaction may be catalyzed by the same or different catalysts, including glycol soluble compounds of titanium or cobalt.

In the manufacture of the polyesters of the present invention a phosphorus and bromine containing bisphenol, or the diacetate or bishydroxyethylation product thereof is copolymerized with the alcoholic and acidic components as exemplified respectively by ethylene glycol and terephthalic acid (or the equivalent dimethyl terephthalate).

It is known that polyethylene terephthalate can be prepared from a suitable methyl ester of terephthalic acid formed by initially reacting methyl alcohol with terephthalic acid. When a methyl ester of terephthalic acid is used as a starting material, it is reacted with ethylene glycol in the presence of a transesterification catalyst by means of an ester interchange reaction. When terephthalic acid itself is used as a starting material it is subjected to a true esterification reaction with ethylene glycol in the presence of what is generally called the first stage catalytic additive.

In either method the resulting reaction product, an ester, is then polycondensed in the presence of a polycondensation catalyst to form polyethylene terephthalate.

In the present process bromine and phosphorus which have been found to exhibit a synergistic effect in fire retardancy when present together, are present in the bisphenol, which is copolymerized with the above-described reactants of the polyester. For example the brominated phosphorus containing bisphenol shown below:

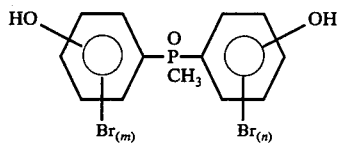

is acetylated by acetic anhydride or ethoxylated by $ClCH_2CH_2OH$ or ethylene oxide.

These compounds undergo polymerization to copolymerize together with the above polyester components without the necessity for any modification of the conventional esterification and polymerization reaction e.g. the use of manganese acetate as a catalyst, and temperatures of from 200°–300° C, preferably 250°–300° C under vacuum, for example 1–30 mm Hg. In this way it is possible to have at least 2 wt. % bromine and from 0.1 to 10 wt. % phosphorus present in the final modified polyester.

The preparation of esters by an ester interchange reaction is generally carried out with a molar ratio of ethylene glycol to dimethyl terephthalate of from about 1:1 to 15:1, respectively, but preferably from about 2:1 to 3:1. The esterification reaction is generally carried out at atmospheric pressure in an inert atmosphere such as nitrogen, initially at a temperature range from about 200°–300° C, but preferably around 200° C to 225° C in the presence or absence of a transesterification catalyst. During the first stage, methyl alcohol is evolved and is continually removed by distillation. Employing procedures heretofore known in the art, the ester interchange portion of the reaction or the first step requires approximately 1 to 4 hours.

Other suitable copolyesters may be employed in the practice of the invention. For example, polymers derived from cyclohexane diglycol terephthalate are useful as is polyethylene-2,6-naphthalate as well as, in general, copolyesters containing terephthalic acid and other acids which contained, based on total acid, preferably more than 75 mol % of terephthalic acid.

In producing polyalkylene terephthalate there is involved the interaction of at least stoichiometric proportions of glycol (preferably ethylene glycol) for molecular proportions of terephthalic acid with the splitting out of water. Subsequent heating of the resulting glycol ester at about 250° C to 280° C under 0.05 to 20 millimeters of mercury pressure absolute results in the production of high polymer with the splitting out of glycol which is removed from the reaction mixture. A desirable procedure for highly polymeric polyalkylene terephthalates is the heating of terephthalic acid derivatives such as ester derivatives of terephthalic acid with at least one glycol. Suitable polyester forming derivatives are aliphatic or aromatic esters of terephthalic acid such as $C_1$ to $C_4$ alkyl esters and/or aryl esters such as those from phenol, cresols and the like. The preferred derivatives are methyl and ethyl terephthalates.

The tetrabromo bisphenol alkyl or aryl phosphine oxide of the present invention is a novel and useful compound.

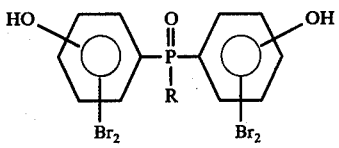

The hydroxyl groups are present in either the para or meta positions, and R is an alkyl radical of 1 to 10 carbon atoms, or an aryl radical of 6 to 10 carbon atoms.

The above compound is made from a phosphonous dihalide,

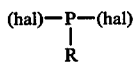

where R is as described above, and a Grignard reagent prepared from a halophenyl alkyl ether such as haloanisol to give anisyl magnesium halide. The bis (anisyl) alkyl or aryl phosphine oxide resulting after oxidation is demethylated to the corresponding bisphenol alkyl or arylphosphine oxide. The para as well as the meta-substituted product or mixtures thereof may be prepared by this procedure. Mixtures of the para and meta compounds are also useful for flame retardant purposes.

Since the compound at this stage does not have bromine present, bromination of the bisphenol phosphine oxide is carried out at a temperature of 0° to 25° C, utilizing elemental bromine as the reactant (no catalyst is necessary). A solvent such as butanol, water or mixtures thereof may be used. The degree of bromination may be such as to introduce 1, 2, 3 or 4 bromine atoms into the molecule. A preferred product is the tetrabromine compound.

The above brominated compounds as well as copolyesters of the present invention are useful flame-retardant materials. The method of testing flame-retardant properties is A.S.T.M. Designation D 2863-70, entitled "Standard Method of Test for Flammability of Plastics Using the Oxygen Index Method".

In the oxygen index (OI) testing procedure the relative flammability of a plastic material such as nylon, or polyethylene terephthalate is determined by measuring the minimum concentration of oxygen in a slowly rising mixture of oxygen and nitrogen that will just support combustion. Consequently the oxygen index expresses such minimum concentration of oxygen, expressed as volume percent, in a mixture of oxygen and nitrogen that will just support combustion.

The test is conducted by burning the material in a test column which is a heat resistant glass tube of 75mm minimum inside diameter and 450mm minimum height. At the bottom of the tube is a bed of glass beads about 100mm deep to mix and distribute the gas mixture. Within the glass tube used as the test column there is a specimen holder to support the treated plastic material, while the apparatus is supplied with oxygen and nitrogen flow and control devices. The apparatus is also provided with an igniter which is a separate tube through which a combustible gas such as natural gas is used to ignite the test specimen: In the present testing program glass scrim supported molded sheets of nylon or polyethylene terephthalate ca. 0.2mm thick and about 25mm by 100mm in size are used as the test specimens which are prepared from nylon or polyethylene terephthalate powder and 1% to 20% by weight of the fire retardant additive. As a result of the molding of the organic polymer e.g. nylon or polyethylene terephthalate, and the additive, an intimate admixture or melt of the molecules of the components is obtained. However copolymers of the ternary components above are also tested in the same way.

In conducting the test, the specimen is clamped in the holder in the test column after which the desired initial concentration of oxygen is introduced to the ignited specimen. A number of tests are conducted to determine the minimum concentration of oxygen that will just support combustion.

The following examples are illustrative of the invention, but are not limitative of the claims of the present patent application.

EXAMPLE 1

A Grignard compound is prepared from 935g (5 mole) of p-bromoanisol and 116.5g (5 gram atoms) of magnesium in tetrahydrofuran. To this solution is added 234g (2 moles) of methylphosphonous dichloride in 500 ml of tetrahydrofuran. After completion of the addition the mixture is refluxed for 2 hours and then hydrolyzed with dilute HCl. The mixture is extracted with $CHCl_3$ to yield 682g of $(CH_3OC_6H_4)_2PCH_3$. The latter is oxidized to the corresponding phosphine oxide by dissolution in water and addition of 285 ml of 30%$H_2O_2$. The water-insoluble product is separated and distilled in vacuo to give 361g (1.3 mole) of $(CH_3OC_6H_4)_2P(O)CH_3$ in 65% yield. The phosphine oxide (252g, 0.41 mole) is demethylated to the corresponding bisphenol by reacting it with 330g (1.3 mole) of borontribromide at −70° C in methylene chloride. Work-up of the reaction solution gives 140g (0.56 mole) of bisphenol methyl phosphine oxide, mp 254° C. A quantity of 74.5g (0.3 mole) of bisphenol methyl phosphine oxide in 230 ml butanol and 90 ml water is brominated by the addition of 192g (1.2 mole) of bromine to give 150 g (0.267 mole) of the tetrabromobisphenol methylphosphine oxide, mp 310° C.

EXAMPLE 2

Using $C_6H_5PCl_2$ in the procedure of example 3 instead of $CH_3PCl_2$ results in tetrabromobisphenol phenylphosphine oxide, mp. 287° C. When this is copolymerized with polyethylene terephthalate to the extent of about 10% by weight relative to the final copolymer the product has 5 wt. % bromine and 0.5 wt. % phosphorous. This product also has flame retardant properties.

EXAMPLE 3

In order to show the improvement brought about by the use of bromine substituted compounds in comparison to the same diol without the bromine-substitution, the following two diols are used in the preparation of polyesters.

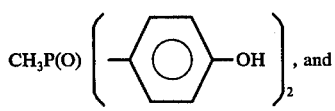

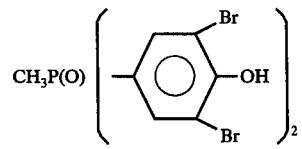

In separate reaction vessels the aforesaid diols are ethoxylated by chloroethanol to give the dihydroxyethoxylated product. Each of the aforesaid reactions is carried out at about 25°–150° C.

The formation of the ester employs the dihydroxyethoxylated compounds, respectively, (although similar results are obtained with the acetylated derivatives to permit ester interchange).

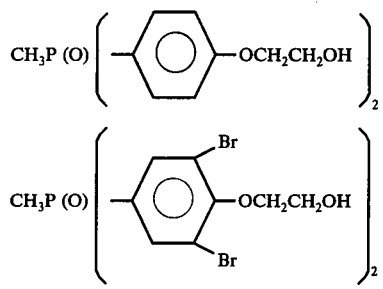

Each of the above is employed in the proportion of 8 grams together with 100 grams of a partially polymerized polyethylene terephthalate having a viscosity [n] of 0.09. The mixture is heated at 240° C with stirring for 30 minutes after which the polymerization is concluded at 280° C under high vacuum (about 1 mm Hg). The final bromine and phosphorus containing polymer has a viscosity [n] of 0.57, and contains 0.33 wt. % phosphorus and 3.20 wt. % bromine.

The two respective polymers are spun and drawn into fibers for testing.

The bromine and phosphorus containing polymer has an oxygen index of 23.1 while the unmodified polyethylene terephthalate based upon the diol (without bromine or phosphorus) has an oxygen index of 20.1. The oxygen index improvement is therefore 3.1 units.

When phosphorus alone is present the oxygen index improvement is only 2.7 units.

When bromine alone is present (e.g. tetrabromo-(2,2-isopropylidene diphenol) bishydroxyethoxylate) the oxygen index improvement is only 2.0 units.

Thus the combination of phosphorus with bromine shows an unexpected superiority.

EXAMPLE 4

When the tetra bromo compound is substituted by the tri bromo compound at about 6 wt. % of the polymer a flame retardant product is also obtained.

Similarly, when the compound

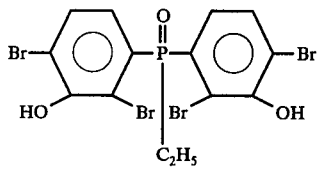

or its bishydroxyethylated product is used at about 10 wt. % in the ternary polymer a flame retardant product is obtained.

What is claimed is:

1. A ternary polyester obtained by the copolymerization at a temperature of 200° C to 300° C of:
   a. an aliphatic alcohol of 2 to 20 carbon atoms, and
   b. an aromatic dicarboxylic acid of 6 to 20 carbon atoms, and
   c. a brominated bisphenol alkyl or aryl phosphine oxide of the formula

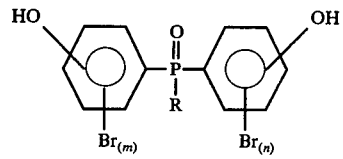

in which the hydroxyl groups are present in either the para or meta positions, $m$ plus $n$ is from 1 to 8, and R is an alkyl radical of 1 to 10 carbon atoms, or an aryl radical of 6 to 10 carbon atoms, the said alcohol and acid being employed in essentially stoichiometric relationship, with the said brominated compound being employed as a partial equivalent of the aforesaid alcohol, to provide from 1 to 20 wt. % of the said brominated compound in the ternary polyester.

2. A ternary polyester obtained by the copolymerization at a temperature of 200° C to 300° C of:
   a. an aliphatic alcohol of 2 to 20 carbon atoms, and
   b. an aromatic dicarboxylic acid of 6 to 20 carbon atoms, and
   c. a brominated bisphenol alkyl or aryl phosphine oxide of the formula

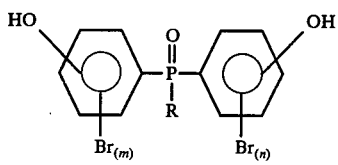

in which the hydroxyl groups are present in either the para or meta positions, $m$ plus $n$ is from 1 to 4, and R is an alkyl radical of 1 to 10 carbon atoms, or an aryl radical of 6 to 10 carbon atoms, the said alcohol and acid being employed in essentially stoichiometric relationship, with the said brominated compound being employed as a partial equivalent of the aforesaid alcohol, to provide from 1 to 20 wt. % of the said brominated compound in the ternary polyester.

3. A ternary polyester obtained by the copolymerization at a temperature of 200° C to 300° C of:
   a. an aliphatic alcohol of 2 to 20 carbon atoms, and
   b. an aromatic dicarboxylic acid of 6 to 20 carbon atoms, and
   c. a brominated bisphenol alkyl or aryl phosphine oxide as the diester of the formula

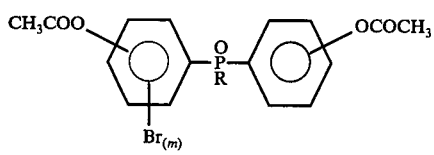

in which the —OCOCH$_3$ groups are present in either the para or meta positions, and $m$ plus $n$ is from 1 to 8, the said alcohol and acid being employed in essentially stoicheometric relationship, with the said brominated compound being employed as a partial equivalent of the aforesaid alcohol, to provide from 1 to 20 wt. % of the said brominated compound in the ternary polyester.

4. A ternary polyester obtained by the copolymerization at a temperature of 200° C to 300° C of:
   a. an aliphatic alcohol of 2 to 20 carbon atoms, and
   b. an aromatic dicarboxylic acid of 6 to 20 carbon atoms, and
   c. a brominated bisphenol alkyl or aryl phosphine oxide as the bishydroxyethyl derivative of the formula

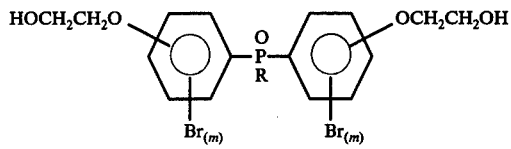

in which the —OCH$_2$CH$_2$OH groups are present in either the para or meta positions, and $m$ plus $n$ is from 1 to 8, the said alcohol and acid being employed in essentially stoichiometric relationship, with the said brominated compound being employed as a partial equivalent of the aforesaid alcohol, to provide from 1 to 20 wt. % of the said brominated compound in the ternary polyester.

5. A polyester obtained by the copolymerization at a temperature of 200° C to 300° C of: terephthalic acid in approximately stoichiometric relationship with ethylene glycol, with the proviso that a part of the glycol is substituted by an equivalent amount of tetrabromo bisphenol methylphosphine oxide to provide from 1 to 20 wt. % of the said tetrabromo bisphenol methylphosphine oxide in the ternary polyester.

6. A polyester obtained by the copolymerization at a temperature of 200° C to 300° C of: terephthalic acid in approximately stoichiometric relationship with ethylene glycol, with the proviso that a part of the glycol is substituted by an equivalent amount of tetrabromo bisphenol phenyl phosphine oxide to provide from 1 to 20 wt. % of the said tetrabromo bisphenol phenyl phosphine oxide in the polyester.

7. A polyester obtained by the copolymerization at a temperature of 200° C to 300° C of: terephthalic acid in approximately stoichiometric relationship with ethylene glycol, with the proviso that a part of the glycol is substituted by an equivalent amount of a brominated bisphenol alkyl or aryl phosphine oxide of the formula

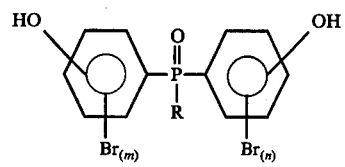

in which the hydroxyl groups are present in either the para or meta positions, $m$ plus $n$ is from 1 to 4, and R is an alkyl radical of 1 to 10 carbon atoms, or an aryl radical of 6 to 10 carbon atoms, the said alcohol and acid being employed in essentially stoichiometric relationship, with the said brominated compound being employed as a partial equivalent of the aforesaid alcohol, to provide from 1 to 20 wt. % of the said brominated compound to provide from 1 to 20 wt. % of the said brominated compound in the ternary polyester.

8. Process for the preparation of ternary polyesters which comprises the copolymerizing of terephthalic acid together with ethylene glycol, at a temperature of 200° C to 300° C, with the proviso that a part of the glycol is substituted by an equivalent amount of a brominated bisphenol alkyl or aryl phosphine oxide of the formula

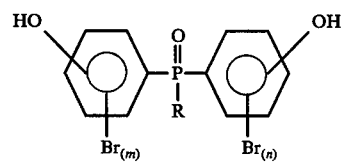

in which the hydroxyl groups are present in either the para or meta positions, $m$ plus $n$ is from 1 to 4, and R is an alkyl radical of 1 to 10 carbon atoms, or an aryl radical of 6 to 10 carbon atoms, the said alcohol and acid being employed in essentially stoichiometric relationship, with the said brominated compound being employed as a partial equivalent of the aforesaid alcohol, to provide from 1 to 20 wt. % of the said brominated compound in the ternary polyester.

* * * * *

UNITED STATES PATENT OFFICE
CERTIFICATE OF CORRECTION

PATENT NO. : 4,087,408
DATED : May 2, 1978
INVENTOR(S) : Kurt Moedritzer

It is certified that error appears in the above-identified patent and that said Letters Patent are hereby corrected as shown below:

Column 8, line 61, Claim 3, in the formula the $Br_{(n)}$ substituent on the second benzene ring has been omitted.

Signed and Sealed this

Third Day of April 1979

[SEAL]

Attest:

RUTH C. MASON
Attesting Officer

DONALD W. BANNER
Commissioner of Patents and Trademarks